United States Patent
Vogt et al.

(10) Patent No.: US 7,968,050 B2
(45) Date of Patent: Jun. 28, 2011

(54) METHOD FOR STERILIZATION OF HYDROGEL CONTACT LENSES

(75) Inventors: Jürgen Vogt, Flueh (CH); Mary Flowers Mowrey-McKee, Alpharetta, GA (US); Dawn Smith, Duluth, GA (US)

(73) Assignee: Novartis AG, Basel (CH)

( * ) Notice: Subject to any disclaimer, the term of this patent is extended or adjusted under 35 U.S.C. 154(b) by 442 days.

(21) Appl. No.: 12/229,111

(22) Filed: Aug. 20, 2008

(65) Prior Publication Data
US 2008/0317625 A1    Dec. 25, 2008

Related U.S. Application Data

(63) Continuation of application No. 11/706,764, filed on Feb. 15, 2007, now abandoned.

(60) Provisional application No. 60/774,984, filed on Feb. 17, 2006.

(51) Int. Cl.
| | |
|---|---|
| *A61L 2/08* | (2006.01) |
| *C09K 3/00* | (2006.01) |
| *C08F 126/02* | (2006.01) |
| *C08F 118/00* | (2006.01) |
| *C08L 53/00* | (2006.01) |
| *G02C 7/04* | (2006.01) |
| *A45C 11/04* | (2006.01) |

(52) U.S. Cl. ....... 422/26; 523/106; 526/301; 526/323.2; 526/320; 351/160 H; 525/93; 510/112; 424/78; 206/5.1; 252/380

(58) Field of Classification Search .................... 422/26; 523/106; 526/301, 323.2, 320; 351/160 H; 525/93; 510/112; 424/78; 206/5.1; 252/380
See application file for complete search history.

(56) References Cited

U.S. PATENT DOCUMENTS

| | | | |
|---|---|---|---|
| 5,882,687 A | 3/1999 | Park et al. ...................... 424/682 |
| 6,143,244 A | 11/2000 | Xia et al. ......................... 422/28 |
| 6,228,323 B1 | 5/2001 | Asgharian et al. ............... 422/28 |
| 6,440,366 B1 | 8/2002 | Salpekar et al. ................. 422/40 |
| 6,531,432 B2 | 3/2003 | Molock et al. ................. 510/112 |
| 6,699,435 B2 | 3/2004 | Salpekar et al. ................. 422/40 |
| 6,867,172 B2 | 3/2005 | Alvarez et al. ................ 510/112 |
| 2004/0142829 A1 | 7/2004 | Tsao et al. ..................... 510/112 |
| 2004/0186028 A1 | 9/2004 | Hu et al. ....................... 510/112 |
| 2005/0056553 A1 | 3/2005 | Matsuzawa et al. ........... 206/5.1 |
| 2005/0119141 A1 | 6/2005 | Quenville et al. ............. 510/112 |

FOREIGN PATENT DOCUMENTS

| | | |
|---|---|---|
| EP | 0 735 097 | 6/2002 |
| EP | 0 986 406 B1 | 8/2002 |
| EP | 1 214 883 | 11/2003 |
| GB | 2 196 255 A | 4/1988 |
| WO | WO 02/45759 A2 | 6/2002 |

OTHER PUBLICATIONS

Standard European Search Report.
Some Properties of Poly(ethylene oxide) in Aqueous Solution, F. E. Bailey, Jr., and R. W. Callard, Journal of Applied Polymer Science, vol. 1, Issue No. 1 pp. 56-62 (1959).

*Primary Examiner* — Jill Warden
*Assistant Examiner* — Monzer R Chorbaji
(74) *Attorney, Agent, or Firm* — Sheng-Hsin Hu; Jian Zhou

(57) ABSTRACT

The present invention provides an aqueous solution for sterilizing and storing ophthalmic devices, preferably a contact lens, made of a hydrogel material, preferably a poly(oxyalkylene)-containing hydrogel material. The solution comprises one or more organic buffer agents, such as a Good buffer or a bis-aminopolyols; an organic tonicity-adjusting agent with multiple hydroxyl groups in an amount sufficient to provide an osmolarity of from about 200 to about 450 mosm/l, wherein the aqueous solution has a pH of from about 5.5 to about 8.5, provided that the aqueous solution include phosphate buffer at a concentration of about 15 mM or less and about 5000 ppm sodium chloride. The present invention also provides a method for sterilizing and storing an ophthalmic device using an aqueous solution of the invention.

12 Claims, No Drawings

METHOD FOR STERILIZATION OF HYDROGEL CONTACT LENSES

This application is a continuation of U.S. patent application Ser. No. 11/706,764, filed Feb. 15, 2007 now abandoned, which claims the benefit under USC §119 (e) of U.S. provisional application No. 60/774,984 filed Feb. 17, 2006, incorporated by reference in its entirety.

The present invention relates to a method for sterilization of ophthalmic devices composed of a hydrogel material, especially a poly(oxyalkylene)-containing polymeric material. More specifically, the present invention relates to a method for sterilizing an ophthalmic device made of a poly(oxyalkylene)-containing polymeric material, wherein the method is characterized by having a reduced autoclave-induced haziness of the ophthalmic device. In addition, the present invention relates to a packaging solution for sterilizing and storing ophthalmic devices made of a hydrogel material, preferably comprising a poly(oxyalkylene)-containing, wherein the solution is capable of reducing autoclave-induced haziness of the poly(oxyalkylene)-containing polymeric material.

BACKGROUND OF THE INVENTION

Because of the biocompatibility of poly(alkyleneglycols), also known as polyalkyl ethers or poly(alkylene oxide), poly(oxyalkylene)-containing polymers can find use in various fields, in particular in biomedical fields, such as, for example, carriers for drug-delivery, artificial tissues, dentrifices, contact lenses, intraocular lenses, and other biomedical devices. However, poly(oxyalkylene)-containing polymers may be susceptible to oxidative degradation and high-temperature-induced or autoclave-induced haziness. Oxidative degradation may cause changes in the properties of an article made from the poly(oxyalkylene)-containing polymers. Autoclave-induced haziness may adversely affect the optical properties of an ophthalmic device, such as, a contact lens or an intraocular lens made of a poly(oxyalkylene)-containing material. Those susceptibilities may limit the applications of poly(oxyalkylene)-containing polymers, in particular, in making ophthalmic devices.

U.S. Patent Application Publication No. 2004/0116564A1 describes a method for stabilizing poly(oxyalkylene)-containing materials. By using such method, a poly(oxyalkylene)-containing polymeric material can be stabilized so that oxidative degradation is significantly reduced. As such, a poly(oxyalkylene)-containing polymeric material can have increased applications, especially in the biomedical field. But, a poly(oxyalkylene)-containing material still may not be suitable for making ophthalmic devices, because ophthalmic devices must be sterilized, typically by autoclave. Autoclave-induced haziness may affect adversely the optical properties of the ophthalmic devices and thereby their primary function in correcting vision deficiencies.

Accordingly, there is still a need for a method for reducing or eliminating the susceptibility to autoclave-induced haziness of poly(oxyalkylene)-containing polymeric materials.

SUMMARY OF THE INVENTION

In one aspect, the present invention provides an aqueous solution for sterilizing and storing an ophthalmic device, wherein the ophthalmic device is made of a poly(oxyalkylene)-containing polymeric material. The aqueous solution of the invention comprises: an $\alpha$-oxo-multi-acid or salt thereof in an amount sufficient to have a reduced susceptibility to oxidation degradation of the poly(oxyalkylene)-containing polymeric material; one or more buffer agents selected from group consisting of TRIS (tris(hydroxymethyl)aminomethane), 2-bis(2-hydroxyethyl)amino-2-(hydroxymethyl)-1,3-propanediol, bis-aminopolyols, triethanolamine, ACES (N-(2-hydroxyethyl)-2-aminoethanesulfonic acid), BES (N,N-Bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS 3-[N-morpholino]-propanesulfonic acid, PIPES (piperazine-N,N'-bis(2-ethanesulfonic acid), TES (N-[Tris(hydroxymethyl)methyl]-2-aminoethanesulfonic acid), and salts thereof; an organic tonicity-adjusting agent in an amount sufficient to provide an osmolarity of from about 200 to about 450 milli-osmole in 1000 ml (unit: mOsm/L), wherein the organic tonicity-adjusting agent is selected from the group consisting of glycerol, sorbitol, xylitol, mannitol, propylene glycol, polyethylene glycol (PEG) with a molecular weight of about 400 Da or less, and mixtures thereof, wherein the aqueous solution has a pH of from about 5.5 to about 8.5, provided that the aqueous solution include phosphate buffer at a concentration of about 15 mM or less and about 5000 ppm or less sodium chloride.

In another aspect, the present invention provides a method for sterilizing and storing ophthalmic devices, comprising the steps of: placing an ophthalmic device in an aqueous solution in a container, wherein the ophthalmic device is made of a poly(oxyalkylene)-containing polymeric material, wherein the aqueous solution comprises: an $\alpha$-oxo-multi-acid or salt thereof in an amount sufficient to have a reduced susceptibility to oxidation degradation of the poly(oxyalkylene)-containing polymeric material; one or more buffer agents selected from group consisting of TRIS (tris(hydroxymethyl)aminomethane), bis-aminopolyols, triethanolamine, ACES (N-(2-hydroxyethyl)-2-aminoethanesulfonic acid), BES (N,N-Bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS 3-[N-morpholino]-propanesulfonic acid, PIPES (piperazine-N,N'-bis(2-ethanesulfonic acid), TES (N-[Tris(hydroxymethyl)methyl]-2-aminoethanesulfonic acid), and salts thereof; an organic tonicity-adjusting agent in an amount sufficient to provide an osmolarity of from about 200 to about 450 milli-osmole in 1000 ml (unit: mosm/l), wherein the organic tonicity-adjusting agent is selected from the group consisting of glycerol, sorbitol, xylitol, mannitol, propylene glycol, polyethylene glycol (PEG) with a molecular weight of about 400 Da or less, and mixtures thereof, wherein the aqueous solution has a pH of from about 5.5 to about 8.5, provided that the aqueous solution include phosphate buffer at a concentration of about 15 mM or less and about 5000 ppm sodium chloride; sealing the container; and autoclaving the sealed container with the ophthalmic device.

In a further aspect, the invention provides an ophthalmic product, comprising a sealed container which has been subjected to sterilization by autoclave, wherein the sealed container includes an aqueous solution and an ophthalmic device immersed in the aqueous solution, wherein the ophthalmic device is composed of a hydrogel material, wherein the aqueous solution includes an organic tonicity-adjusting agent in an amount sufficient to provide an osmolarity of from about 200 to about 450 milli-osmole in 1000 ml (unit: mosm/l) and one or more buffer agents selected from group consisting of tris-(hydroxymethyl)aminomethane) (TRIS), bis-aminopolyols, triethanolamine, N-(2-hydroxyethyl)-2-aminoethanesulfonic acid (ACES), N,N-Bis(2-hydroxyethyl)-2-aminoethanesulfonic acid (BES), 4-(2-hydroxyethyl)-1- piperazineethanesulfonic acid (HEPES), 2-(N-morpholino) ethanesulfonic acid (MES), 3-[N-morpholino]-propanesulfonic acid (MOPS), piperazine-N,N'-bis(2-ethanesulfonic acid) (PIPES), N-tris(hydroxymethyl) methyl-2-aminoethanesulfonic acid (TES), and salts thereof, wherein the organic tonicity-adjusting agent is selected from the group consisting of glycerol, sorbitol, xylitol, mannitol, propylene glycol, polyethylene glycol (PEG) with a molecular weight of about 400 Da or less, and mixtures thereof, wherein the aqueous solution has a pH of from about 5.5 to about 8.5, wherein the aqueous solution include phosphate buffer at a concentration of about 15 mM or less and about 5000 ppm sodium chloride so that the solution imparts a reduced autoclave-induced haziness to the ophthalmic device, wherein the reduced autoclave-induced haziness is characterized by having less than about 10% autoclave-induced reduction in light transmissibility in the visible wavelength range of 400 to 800 nm, typically measured at 500 nm.

In still a further aspect, the present invention provides a method for sterilizing and storing ophthalmic devices, comprising the steps of: placing an ophthalmic device in an aqueous solution in a container, wherein the ophthalmic device is composed of a hydrogel material, wherein the aqueous solution includes an organic tonicity-adjusting agent in an amount sufficient to provide an osmolarity of from about 200 to about 450 milli-osmole in 1000 ml (unit: mosm/l) and one or more buffer agents selected from group consisting of tris-(hydroxymethyl)aminomethane) (TRIS), bis-aminopolyols, triethanolamine, N-(2-hydroxyethyl)-2-aminoethanesulfonic acid (ACES), N,N-Bis(2-hydroxyethyl)-2-aminoethane-sulfonic acid (BES), 4-(2-hydroxyethyl)-1-piperazineethanesulfonic acid (HEPES), 2-(N-morpholino)ethanesulfonic acid (MES), 3-[N-morpholino]-propanesulfonic acid (MOPS), piperazine-N,N'-bis(2-ethanesulfonic acid) (PIPES), N-tris(hydroxymethyl)methyl-2-aminoethanesulfonic acid (TES), and salts thereof, wherein the organic tonicity-adjusting agent is selected from the group consisting of glycerol, sorbitol, xylitol, mannitol, propylene glycol, polyethylene glycol (PEG) with a molecular weight of about 400 Da or less, and mixtures thereof, wherein the aqueous solution has a pH of from about 5.5 to about 8.5, wherein the aqueous solution include phosphate buffer at a concentration of about 15 mM or less and about 5000 ppm sodium chloride so that the solution imparts a reduced autoclave-induced haziness to the ophthalmic device, wherein the reduced autoclave-induced haziness is characterized by having less than about 10% autoclave-induced reduction in light transmissibility at 500 nm.

These and other aspects of the invention will become apparent from the following description of the preferred embodiments. As would be obvious to one skilled in the art, many variations and modifications of the invention may be effected without departing from the spirit and scope of the novel concepts of the disclosure.

DETAILED DESCRIPTION OF THE PREFERRED EMBODIMENTS

Reference now will be made in detail to the embodiments of the invention. It will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art.

The present invention generally relates to an aqueous solution and a method for sterilizing and storing ophthalmic devices made of a hydrogel material, in particular, made of a poly(oxyalkylene)-containing hydrogel material. The invention is partly based on the discovery that, by using organic buffer agents in the solution instead of inorganic buffer agent (e.g., phosphate buffer) to maintain a physiological pH (from about 5 to about 9) and by using one or more organic tonicity-adjusting agent instead of the conventional tonicity agent (i.e., NaCl) to adjust the osmolarity of the solution, one can substantially reduce autoclave-induced haziness of a hydrogel material, especially a poly(oxyalkylene)-containing polyurea contact lenses. It is believed that the autoclave-induced haziness in poly(ethylene glycol)-urea (PEG-urea) lenses may be caused by phase separation and that the phase separation may be caused by a combination of microsyneresis (i.e., water ejection from the hydrogel upon heating) and salting out phenomenon (coagulation of PEG chains caused by certain ionic species in the saline). It is also believed that the separated phases during autoclaving may become permanent and thereby imparting a permanent haziness to the PEG-urea lenses. It is further believed that certain ions, especially anions including, e.g., phosphate, citrate, chloride, may cause the phase separation of a hydrogel material, especially a poly(oxyalkylene)-containing hydrogel material. By replacing phosphate buffer with one or more organic buffers and using a tonicity-adjusting agent with multi-hydroxy groups instead of sodium chloride to provide a physiological osmolarity to a solution which is used for sterilizing and storing an ophthalmic device made of a hydrogel material, especially a poly(oxyalkylene)-containing hydrogel material, one can substantially reduce the autoclave-induced haziness of the hydrogel material. Moreover, an organic buffer, e.g., TRIS, may lower the pH of a solution as the temperature increases.

An "ophthalmic device", as used herein, refers to a contact lens (hard or soft), an intraocular lens, a corneal onlay, other ophthalmic and biomedical devices (e.g., stents, or the like) used on or about the eye or ocular vicinity or in the human body.

A "hydrogel" refers to a polymeric material which can absorb at least 10 percent by weight of water when it is fully hydrated. Generally, a hydrogel material is obtained by polymerization or copolymerization of at least one hydrophilic monomer in the presence of or in the absence of additional monomers and/or macromers. In accordance with the invention, a hydrogel includes silicone hydrogels and non-silicone hydrogels.

A "silicone hydrogel" refers to a hydrogel obtained by copolymerization of a polymerizable composition comprising at least one silicone-containing monomer or at least one silicone-containing macromer. A "non-silicone hydrogel" refers to a hydrogel obtained by copolymerization of a polymerizable composition free of any silicone-containing monomer or macromer.

A "monomer" means a low molecular weight compound that can be polymerized. Low molecular weight typically means average molecular weights less than 700 Daltons.

A "macromer" refers to a medium and high molecular weight compound or polymer that contains functional groups capable of undergoing further polymerizing/crosslinking reactions. Medium and high molecular weight typically means average molecular weights greater than 700 Daltons.

A "polymer" means a material formed by polymerizing/crosslinking one or more monomers.

A "prepolymer" refers to a starting polymer which can be cured (e.g., crosslinked and/or polymerized) actinically or thermally or chemically to obtain a crosslinked and/or polymerized polymer having a molecular weight much higher than the starting polymer.

As used herein, "actinically" in reference to curing of a polymerizable composition or material means that the curing (e.g., crosslinked and/or polymerized) is performed by actinic irradiation, such as, for example, UV and visible irradiation, ionizing radiation (e.g. gamma ray, e beam, or X-ray irradiation), and microwave irradiation.

According to one embodiment of the present invention, a poly(oxyalkylene)-containing polymeric material can be any polymer having at least one unit of formula (1)

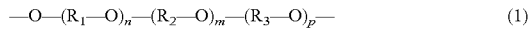

$$—O—(R_1—O)_n—(R_2—O)_m—(R_3—O)_p— \quad (1)$$

wherein $R_1$, $R_2$, and $R_3$, independently of one other, are each linear or branched $C_2$-$C_4$-alkylene, and n, m and p, independently of one another, are each a number from 0 to 100, wherein the sum of (n+m+p) is 5 to 100.

Examples of a polymer containing at least one unit of formula (I) include, but are not limited to, (1) a hydroxy terminated (diols) poly(alkylene glycol); (2) a poly(alkylene glycol) in which the terminal diols have been converted to amines (i.e., an amine terminated poly(alkylene glycol)); (3) a poly(alkylene glycol) in which the terminal diols have been esterified with organic acids such as, for example, acetic acid, acrylic acid, or methacrylic acid; (4) a polyester obtained by esterification of the terminal diols of a poly(alkylene glycol) with organic monoacids or diacids such as, for example, glutaric or adipic acids; (5) a polyamide obtained by reacting an amine terminated pol(alkylene glycol) with organic monoacids or diacids acids such as, for example, glutaric or adipic acids; (6) a polyurethane which is the copolymerization product of a mixture comprising one or more hydroxy-terminated poly(alkylene glycols) and one or more di- or polyisocyanates; (7) a polyurea which is the copolymerization product of a mixture comprising one or more amine-terminated poly(alkylene glycols) and one or more di- or multi-isocyanates. The above examples have been given as a means of illustrating the aspects of the invention and are not limiting in any way.

A poly(oxyalkylene)-containing polymeric material can also be an interpenetrating or semi-interpenetrating polymer network. An "interpenetrating polymer network" (IPN) as used herein refers broadly to an intimate network of two or more polymers at least one of which is either synthesized and/or crosslinked in the presence of the other(s). Techniques for preparing IPN are known to one skilled in the art. For a general procedure, see U.S. Pat. Nos. 4,536,554, 4,983,702, 5,087,392, and 5,656,210, the contents of which are all incorporated herein by reference. The polymerization is generally carried out at temperatures ranging from about room temperature to about 200° C.

Exemplary interpenetrating polymer networks are interpenetrating polyurea/polyacrylic networks disclosed in EP 0735097 B1. Such interpenetrating polyurea/polyacrylic networks are formed by polymerizing a reactive mixture comprising: (a) at least one amine-terminated poly(alkylene glycol); (b) an organic di- or polyisocyanate which reacts with (a) to form a polyurea network; (c) an acrylic ester; (d) a free radical initiator to polymerize (c) to form a polyacrylic network; and (e) a triamine to crosslink (a).

Exemplary poly(alkylene glycol)s include, but are not limited to, a poly(ethylene glycol), a poly(1-propylene glycol), a poly(2-propylene glycol), a poly(ethylene glycol)/poly(propylene glycol) block polymer, a poly(ethylene glycol)/poly(propylene glycol)/poly(butylene glycol) block polymer, a polytetrahydrofuran, a poloxamer, and the like.

Examples of preferred poly(oxyalkylene)-containing hydrogel material are those obtained by crosslinking a crosslinkable polyurea polymer described in U.S. Pat. No. 6,479,587 and U.S. Published Patent Application No. 2005/0113549 A1, herein incorporated by references in their entireties. Such crosslinkable polyurea polymer can be prepared by introducing ethylenically unsaturated groups into a polyurea which is the copolymerization product of a reaction mixture including at least one amine-terminated poly(alkylene glycol) and an organic di- or polyisocyanate.

Exemplary ethylenically unsaturated groups include without limitation acryloyl, methacryloyl, allyl, vinyl, styrenyl, or other C=C containing groups.

In one aspect, the present invention provides an aqueous solution for sterilizing and storing an ophthalmic device, wherein the ophthalmic device is made of a poly(oxyalkylene)-containing polymeric material. The aqueous solution of the invention comprises: an α-oxo-multi-acid or salt thereof in an amount sufficient to have a reduced susceptibility to oxidation degradation of the poly(oxyalkylene)-containing polymeric material; one or more buffer agents selected from group consisting of TRIS (tris(hydroxymethyl)aminomethane), bis-aminopolyols, triethanolamine, ACES (N-(2-hydroxyethyl)-2-aminoethanesulfonic acid), BES (N,N-Bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS 3-[N-morpholino]-propanesulfonic acid, PIPES (piperazine-N,N'-bis (2-ethanesulfonic acid), TES (N-[Tris(hydroxymethyl)methyl]-2-aminoethanesulfonic acid), and salts thereof; an organic tonicity-adjusting agent in an amount sufficient to provide an osmolarity of from about 200 to about 450 milliosmole in 1000 ml (unit: mosm/l), wherein the organic tonicity-adjusting agent is selected from the group consisting of glycerol, sorbitol, xylitol, mannitol, propylene glycol, polyethylene glycol (PEG) with a molecular weight of about 400 Da or less, and mixtures thereof, wherein the aqueous solution has a pH of from about 5.5 to about 8.5, provided that the aqueous solution include phosphate buffer at a concentration of about 15 mM or less and about 5000 ppm sodium chloride.

In accordance with the invention, an aqueous solution of the invention is ophthalmically safe. The term "ophthalmically safe" with respect to an aqueous solution for sterilizing and storing contact lenses is meant that a contact lens stored in the solution is safe for direct placement on the eye without rinsing, that is, the solution is safe and sufficiently comfortable for daily contact with the eye via a contact lens. An ophthalmically safe solution has a tonicity and pH that is compatible with the eye and comprises materials, and amounts thereof, that are non-cytotoxic according to international ISO standards and U.S. FDA regulations.

The term "compatible with the eye" means a solution that may be in intimate contact with the eye for an extended period of time without significantly damaging the eye and without significant user discomfort.

Exemplary α-oxo-multi-acids or biocompatible salts thereof include without limitation citric acid, 2-ketoglutaric acid, or malic acid or biocompatible (preferably ophthalmically compatible) salts thereof. More preferably, an α-oxo-multi-acid of the present invention is citric or malic acid or biocompatible (preferably ophthalmically compatible) salts thereof (e.g., sodium, potassium, or the like).

A "stabilized poly(oxyalkylene)-containing polymeric material" means that a poly(oxyalkylene)-containing polymeric material, which is prepared from a composition comprising a stabilizer and/or subjected to a sterilization treatment in a solution containing the stabilizer, is less susceptible to oxidative degradation (i.e., characterized by the amount of detectable formic acid and optionally other degradation by-products in a stabilized poly(oxyalkylene)-containing polymeric material being 80% or less, preferably 65% or less, more preferably 50% or less, of that detected in a non-stabilized poly(oxyalkylene)-containing polymeric material). A "non-stabilized poly(oxyalkylene)-containing polymeric material" means that a poly(oxyalkylene)-containing polymeric material, which is prepared from a composition without the stabilizer and/or subjected to a sterilization treatment in a solution without the stabilizer.

"Improve the stability of a poly(oxyalkylene)-containing polymeric material" means that the susceptibility to oxidative degradation of a poly(oxyalkylene)-containing polymeric material, which is prepared from a composition comprising a stabilizer and/or subjected to a sterilization treatment in a solution containing the stabilizer, is reduced (characterized by the amount of detectable formic acid and optionally other degradation by-products in a stabilized poly(oxyalkylene)-containing polymeric material being 80% or less, preferably 65% or less, more preferably 50% or less, of that detected in a non-stabilized poly(oxyalkylene)-containing polymeric material).

The contact lenses sterilized and stored in an aqueous solution of the invention can have a low susceptibility to oxidative degradation, characterized by having a reduced amount of formic acid and/or other degradation by-products detected in the contact lenses. They may have a longer shelf life. Moreover, because of reduction in the formation of formic acid or formate, the contact lenses obtained according to the invention may not cause irritation to the eyes of a wearer.

Of course, all the above-mentioned advantages apply not only to contact lenses, but also to other molded articles according to the invention, for example, an implantable medical device obtained according to the invention. The total of the different advantageous aspects during production of the molded articles according to the invention leads to the suitability of the molded articles in particular as mass-produced articles, for example, as contact lenses which are for daily use and/or for weekly use and/or for continuous wear.

Preferably, a buffer agent is TRIS (tris(hydroxymethyl) aminomethane) or bis-aminopolyols.

The preferred bis-aminopolyols have formula (I)

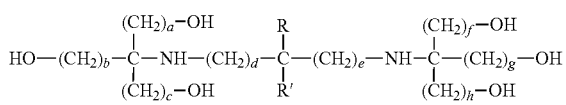

(I)

wherein a, b, c, d, e, f, g, and h are independently an integer from 1 to 6; and R and R' are independently selected from the group consisting of —H, —CH$_3$, —(CH$_2$)$_{2-6}$—H, and —(CH$_2$)$_{1-6}$—OH. In the present invention, the buffering agents described by formula (I) may be provided in the form of various water-soluble salts. A most preferred bis-aminopolyol is 1,3-bis(tris[hydroxymethyl]methylamino)propane (bis-TRIS-propane). BIS-TRIS propane is described under biological buffers in Biochemicals and Reagents, Sigma-Aldrich Co., 2000-2001 edition. The specific structure of bis-TRIS-propane is shown in formula II.

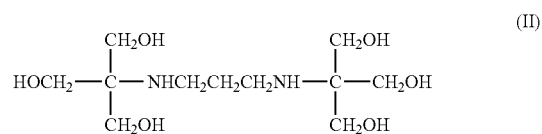

(II)

The dissociation constants for this dibasic compound are pKa$_1$=6.8 and pKa$_2$=9.5 which renders aqueous solutions of this compound useful as a buffering agent in a broad pH range from about 6.3 to 9.3. bis-TRIS-propane at a concentrations used in this invention is harmless to the eye and to known contact lens materials and is, therefore, ophthalmically compatible.

Preferably, the solutions of the present invention have a low concentration of phosphate ions, more preferably substantially free of phosphate ions. Solutions having about 15 mM or less phosphate ion and about 5000 ppm chloride ion can have significantly reduced autoclave induced haziness of a hydrogel material, especially a poly(oxyalkylene)-containing hydrogel material. Previously known solutions generally had very high concentrations of both phosphate ions and chloride ions, to maintain the solution pH and achieve a desired osmolarity.

In accordance with the invention, the organic tonicity-adjusting agent is present in an amount sufficient to provide the aqueous solution a osmolarity of from about 200 to about 450 mosm/l, preferably from about 250 to 350 mosm/l. Preferably, the concentration of the organic tonicity-adjusting agent is from about 0.1% to about 10%, more preferably from about 0.5% to about 5%. The organic tonicity-adjusting agent is preferably glycerol, sorbitol, xylitol, or mixture thereof.

Reduction in autoclave-induced haziness of an ophthalmic device can be characterized by light transmissibility around 500 nm, preferably by light scattering, after autoclave in comparison with that before autoclave. Preferably, an ophthalmic device under test is a contact lens having an optical power of typically from +6 diptors to −10 diopters. A hydrogel material under test preferably is a film having a thickness of about 250 µm.

In one embodiment, a solution of the invention preferably imparts a reduced autoclave-induced haziness of a hydrogel ophthalmic device, wherein the reduced autoclave-induced haziness is characterized by having less than about 10%, preferably less than about 5%, even more preferably less than about 3% autoclave-induced reduction in light transmissibility at 500 nm.

The percentage of autoclave-induced reduction in light transmissibility at 500 nm ($\Delta T_{500nm}$%) is defined as $$\Delta T_{500\ nm} / \% = \frac{T_0(500\ nm) - T_1(500\ nm)}{T_0(500\ nm)} \cdot 100$$

in which T$_0$(500 nm) and T$_1$(500 nm) represent the light transmissibilities at 500 nm before autoclave and after autoclave respectively.

A solution of the invention may further comprise a lubricant. "Lubricants" as used herein refer to any compounds or materials which can enhance surface wettability of a contact lens and/or the eye or reduce the frictional character of the contact lens surface. Examples of lubricants include without limitation mucin-like materials and hydrophilic polymers.

Exemplary mucin-like materials include without limitation polyglycolic acid, polylactides, collagen, and gelatin. A mucin-like material may be used to alleviate dry eye syndrome. The mucin-like material preferably is present in effective amounts.

Exemplary hydrophilic polymers include, but are not limited to, polyvinylalcohols (PVAs), polyamides, polyimides, polylactone, a homopolymer or copolymer of a vinyl lactam in the presence or in the absence of one or more hydrophilic vinylic comonomers (e.g., polyvinylpyrrolidone of a molecular weight of up to 1,500,000, a copolymer of a molecular weight of up to 1,500,000 of vinylpyrrolidone with another vinyl monomer), a homopolymer of acrylamide or methacrylamide, a high molecular weight PEG (with a molecular weight of greater than about 50000 Da, a copolymer of acrylamide or methacrylamide with one or more hydrophilic vinylic monomers, mixtures thereof. The number-average molecular weight $M_n$ of a hydrophilic polymer is at least 40000 daltons, preferably at least 80000 daltons, more preferably at least 100000 daltons, even more preferably at least 250000 daltons.

A solution of the invention preferably has a surface tension of about 60 mN/m or smaller. It may optionally comprises a surfactant to lower its surface tension. By lowering the surface tension of the aqueous solution, one can minimize the formation of meniscus on the wall of a container containing the aqueous solution and an ophthalmic device.

Any suitable known surfactants can be used in the invention. Examples of suitable surfactants include, but are not limited to poloxamers under the tradename Pluronic from BASF Corp. (Pluronic™ and Pluronic-R™) which are non-ionic surfactants consisting of block copolymers of propylene oxide and ethylene oxide; poloxamine which is a block copolymer derivative of ethylene oxide and propylene oxide combined with ethylene diamine; tyloxapol, which is 4-(1,1,3,3-tetramethylbutyl)phenol polymer with formaldehyde and oxirane; ethoxylated alkyl phenols, such as various surface active agents available under the tradenames TRITON (Union Carbide, Tarrytown, N.Y., USA) and IGEPAL (Rhone-Poulenc, Cranbury, N.J., USA); polysorbates such as polysorbate 20, including the polysorbate surface active agents available under the tradename TWEEN (ICI Americas, Inc., Wilmington, Del., USA.); alkyl glucosides and polyglucosides such as products available under the tradename PLANTAREN (Henkel Corp., Hoboken, N.J., USA); polyethoxylated castor oils commercially available from BASF under the trademark CREMAPHOR; and PVP.

Preferred surfactants include homopolymers of polyethylene glycol or polyethyleneoxide, and certain poloxamers such as materials commercially available from BASF under the tradenames PLURONIC® 17R4, PLURONIC® F-68NF, PLURONIC® F68LF, and PLURONIC® F127, with PLURONIC® F-68NF (National Formulary grade) being the most preferred. More preferably, a combination of PLURONIC® 17R4 and PLURONIC® F127 is used. When present, poloxamers may be employed at from about 0.001% to about 5% by weight, preferably from about 0.005% to about 1% by weight, more preferably from about 0.05% to about 0.6% by weight.

A solution of the invention may further comprise one or more substances selected from the group consisting of ethylenediaminetetraacetic acid (EDTA), alginates, hyaluronic acid, alpha-dextrin, maltose, amylose, methyl cellulose (MC), ethyl cellulose, hydroxymethylcellulose, hydroxyethyl cellulose (HEC), hydroxypropylcellulose, hydroxypropylmethyl cellulose (HPMC).

In another aspect, the present invention provides a method for sterilizing and storing ophthalmic devices, comprising the steps of: placing an ophthalmic device in an aqueous solution in a container, wherein the ophthalmic device is made of a poly(oxyalkylene)-containing polymeric material, wherein the aqueous solution comprises: an α-oxo-multi-acid or salt thereof in an amount sufficient to have a reduced susceptibility to oxidation degradation of the poly(oxyalkylene)-containing polymeric material; one or more buffer agents selected from group consisting of TRIS (tris(hydroxymethyl) aminomethane), bis-aminopolyols, triethanolamine, ACES (N-(2-hydroxyethyl)-2-aminoethanesulfonic acid), BES (N,N-Bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS 3-[N-morpholino]-propanesulfonic acid, PIPES (piperazine-N,N'-bis(2-ethanesulfonic acid), TES (N-[Tris(hydroxymethyl)methyl]-2-aminoethanesulfonic acid), and salts thereof; an organic tonicity-adjusting agent in an amount sufficient to provide an osmolarity of from about 200 to about 450 milli-osmole in 1000 ml (unit: mosm/l), wherein the organic tonicity-adjusting agent is selected from the group consisting of glycerol, sorbitol, xylitol, mannitol, propylene glycol, polyethylene glycol (PEG) with a molecular weight of about 400 Da or less, and mixtures thereof, wherein the aqueous solution has a pH of from about 5.5 to about 8.5, provided that the aqueous solution include phosphate buffer at a concentration of about 15 mM or less and about 5000 ppm sodium chloride; sealing the container; and autoclaving the sealed container with the ophthalmic device.

Above described various embodiments and preferred embodiments of an aqueous solution of the invention can be used in this aspect of the invention.

In a further aspect, the invention provides an ophthalmic product, comprising a sealed container which has been subjected to sterilization by autoclave, wherein the sealed container includes an aqueous solution and an ophthalmic device immersed in the aqueous solution, wherein the ophthalmic device is composed of a hydrogel material, wherein the aqueous solution includes an organic tonicity-adjusting agent in an amount sufficient to provide an osmolarity of from about 200 to about 450 milli-osmole in 1000 ml (unit: mosm/l) and one or more buffer agents selected from group consisting of tris-(hydroxymethyl)aminomethane) (TRIS), bis-aminopolyols, triethanolamine, N-(2-hydroxyethyl)-2-aminoethanesulfonic acid (ACES), N,N-Bis(2-hydroxyethyl)-2-aminoethanesulfonic acid (BES), 4-(2-hydroxyethyl)-1-piperazineethanesulfonic acid (HEPES), 2-(N-morpholino)ethanesulfonic acid (MES), 3-[N-morpholino]-propanesulfonic acid (MOPS), piperazine-N,N'-bis(2-ethanesulfonic acid) (PIPES), N-tris(hydroxymethyl)methyl-2-aminoethanesulfonic acid (TES), and salts thereof, wherein the organic tonicity-adjusting agent is selected from the group consisting of glycerol, sorbitol, xylitol, mannitol, propylene glycol, polyethylene glycol (PEG) with a molecular weight of about 400 Da or less, and mixtures thereof, wherein the aqueous solution include phosphate buffer at a concentration of about 15 mM or less and about 5000 ppm sodium chloride so that the solution imparts a reduced autoclave-induced haziness to the ophthalmic device, wherein the reduced autoclave-induced haziness is characterized by having less than about 10% autoclave-induced reduction in light transmissibility at 500 nm.

Above described various embodiments and preferred embodiments of an aqueous solution of the invention can be used in this aspect of the invention.

In still a further aspect, the present invention provides a method for sterilizing and storing ophthalmic devices, comprising the steps of: placing an ophthalmic device in an aqueous solution in a container, wherein the ophthalmic device is composed of a hydrogel material, wherein the aqueous solution includes an organic tonicity-adjusting agent in an amount sufficient to provide an osmolarity of from about 200 to about 450 milli-osmole in 1000 ml (unit: mosm/l) and one or more buffer agents selected from group consisting of tris-(hydroxymethyl)aminomethane) (TRIS), bis-aminopolyols, triethanolamine, N-(2-hydroxyethyl)-2-aminoethanesulfonic acid (ACES), N,N-Bis(2-hydroxyethyl)-2-aminoethanesulfonic acid (BES), 4-(2-hydroxyethyl)-1-piperazineethanesulfonic acid (HEPES), 2-(N-morpholino)ethanesulfonic acid (MES), 3-[N-morpholino]-propanesulfonic acid (MOPS), piperazine-N,N'-bis(2-ethanesulfonic acid) (PIPES), N-tris(hydroxymethyl)methyl-2-aminoethanesulfonic acid (TES), and salts thereof, wherein the organic tonicity-adjusting agent is selected from the group consisting of glycerol, sorbitol, xylitol, mannitol, propylene glycol, polyethylene glycol (PEG) with a molecular weight of about 400 Da or less, and mixtures thereof, wherein the aqueous solution has a pH of from about 5.5 to about 8.5, wherein the aqueous solution include phosphate buffer at a concentration of about 15 mM or less and about 5000 ppm sodium chloride so that the solution imparts a reduced autoclave-induced haziness to the ophthalmic device, wherein the reduced autoclave-induced haziness is characterized by having less than about 10% autoclave-induced reduction in light transmissibility at 500 nm; sealing the container; and autoclaving the sealed container with the ophthalmic device.

Above described various embodiments and preferred embodiments of an aqueous solution of the invention can be used in this aspect of the invention.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

EXAMPLE 1

Preparation of PEG-Urea Prepolymer. Place 400 g of tetrahydrofuran (THF), 250 g of water, 84 amine group milliequivalents (meq) of Jeffamine® XTJ501 (Hunstman Chemicals), 50 amine group meq of Jeffamine® XTJ502 (Hunstman Chemicals) and 26.8 amine group meq of bis-hexamethylenetriamine (Aldrich Chemicals) into a jacketed 1 L reactor and cool to an internal temperature of 0 to 5° C. with agitation. A solution containing 100 isocyanate group meq of isophorone diisocyanate (Aldrich Chemicals) and 26.8 isocyanate group meq of VESTANAT® T1890/100 (Degussa Chemicals) in about 80 g of THF is added dropwise, with stirring, over a period of approximately 30 minutes. Stir the reaction mixture for a further 30 minutes whilst maintaining an internal temperature of 0 to 5° C. Three additions of 21.5 g of sodium carbonate (20% aqueous), followed by 3.4 g of acryloyl chloride (Aldrich Chemicals) are made with approximately 30 minutes between each addition, whilst maintaining an internal temperature below 10° C. Stir the reaction mixture for a further 30 minutes whilst allowing the internal temperature to reach ambient. The reaction mixture is filtered over 17 µm sintered glass filter. The product is then concentrated on a rotary evaporator to afford a solution essentially free of THF. The solution is ultrafiltered over a 1-kDa membrane until the conductivity of the permeate measures below 50 µS/cm. The solution is further purified by passing the solution through a 0.45 µm Teflon membrane under pressure. The solution is stabilized with 20-200 ppm of hydroxyl-TEMPO.

EXAMPLE 2

Preparation of PEG-Urea Prepolymer. Place 500 g of tetrahydrofuran (THF), 250 g of water, 88 amine group milliequivalents (meq) of Jeffamine® XTJ501 (Hunstman Chemicals), 8 amine group meq of Jeffamine® XTJ502 (Hunstman Chemicals), 64 amine group meq of 2-(2-aminoethylamino) ethanol (AEAE), and 12 amine group meq of bis-hexamethylenetriamine (HMTA) (Aldrich Chemicals) into a jacketed 1 L reactor and cool to an internal temperature of 0 to 5° C. with agitation. A solution containing 155 isocyanate group meq of isophorone diisocyanate (Aldrich Chemicals) in THF is added dropwise, with stirring, over a period of approximately 30 minutes. Stir the reaction mixture for a further 30 minutes whilst maintaining an internal temperature of 0 to 5° C. Three additions of 21.5 g of sodium carbonate (20% aqueous), followed by 3 mL of acryloyl chloride (Aldrich Chemicals) are made with approximately 30 minutes between each addition, whilst maintaining an internal temperature below 10° C. Stir the reaction mixture for a further 30 minutes whilst allowing the internal temperature to reach ambient. The reaction mixture is filtered over 17 µm sintered glass filter. The product is then concentrated on a rotary evaporator to afford a solution essentially free of THF. The solution is ultrafiltered over a 1 kDa membrane until the conductivity of the permeate measures below 30 µS/cm. The solution is further purified by passing the solution through a 0.45 µm pore size hydrophilic polyether sulfone membrane under pressure. The solution is stabilized with 20-200 ppm of hydroxyl-TEMPO.

EXAMPLE 3

Films of about 250 microns in thickness are prepared from an aqueous formulation containing about 44% of PEG-urea prepolymer prepared in Example 2, 0.125% by weight of Irgacure 2959 and water. The polymerization is carried out in a glass/quartz flat mold pair, using the appropriate spacer ring to achieve a flat disk of 250 micron thickness.

UV light is impinged on the mold arrangement. The light source is a UV-IQ400 manufactured by Dr. Groebel UV Electronic GmbH, fitted with a Phillips HPA-400/30S bulb. Light from the source is directed down a light guide and through a WG305 cut-off filter manufactured by Schott Glass. The intensity of light that passes through this optical arrangement is measured with a RM-12 radiometer manufactured by Dr. Groebel Electronic GmbH and calibrated to the manufacture's standard. The irradiation dose is controlled by using a fixed intensity of light and modulating the exposure time through the use of an automated shutter arrangement. The cure energy density (mJ/cm$^2$) determined is used to cure each respective PEG-Urea polymer formulation.

EXAMPLE 4

Contact lenses are prepared from an aqueous formulation containing about 32% or 44%, respectively, of PEG-urea prepolymer prepared in Example 1 or 2, an appropriate amount of mold release agent, 0.125 to 0.15% (relative to prepolymer) by weight of Irgacure 2959 and water.

Preparation of Contact Lenses. Typically 40-65 mg of the above prepared formulation is charged into the cavity of a female mold half and a male mold half is placed on top of the female mold half to form a mold assembly which is disclosed in detail in U.S. Pat. No. 6,203,909 B1, herein incorporated by reference in its entirety. Molds for making Focus® DAI-LIES® are used UV light is impinged on the mold arrangement. The light source is a UV-IQ400 manufactured by Dr. Groebel UV Electronic GmbH, fitted with a Phillips HPA-400/30S bulb. Light from the source is directed down a light guide and through a WG305 cut-off filter manufactured by Schott Glass. The intensity of light that passes through this optical arrangement is measured with a RM-12 radiometer manufactured by Dr. Groebel Electronic GmbH and calibrated to the manufactures' standard. The irradiation dose is controlled by using a fixed intensity of light and modulating the exposure time through the use of an automated shutter arrangement.

The mold is opened and the contact lens removed, washed with deionized water to remove excess unreacted formulation.

EXAMPLE 5

Aqueous solutions are prepared to have different compositions shown in Table 1.

TABLE 1

| solution DI water | [citrate] mM | [Pi]* mM | [TRIS] mM | [bTp] mM | [NaCl] % | [glycerol] % | [sorbitol] % |
|---|---|---|---|---|---|---|---|
| 1 | 10 | 20 | | | | 2.1 | |
| 2 | 10 | 20 | | | | | 4.2 |
| 3 [1] | 10 | 20 | | | 0.7 | | |
| 4 [1] | 40 | | | | 0.7 | | |
| 5 [2] | 10 | 14 | 29 | | | 2.1 | |
| 6 | 10 | 14 | 29 | | | | 4.2 |
| 7 | 10 | 14 | 29 | | 0.7 | | |
| 8 | 10 | 14 | 29 | | | 2.1 | |
| 9 [3] | 10 | 14 | 29 | | | 2.1 | |
| 10 [4] | 10 | 13 | 29 | | | 2.1 | |
| 11 [5] | 10 | | 42 | | 0.7 | | |
| 12 [5] | 10 | | 42 | | | 2.1 | |
| 13 [6] | 10 | 13 | 29 | | | 2.2 | |
| 14 [7] | 10 | 14 | 29 | | | 2.1 | |
| 15 [8] | 10 | | 39 | | | 2.1 | |
| 16 [8] | 10 | | 39 | | 0.7 | | |
| 17 [9] | 10 | | | 12 | | 2.5 | |
| 18 [10] | 10 | 20 | | | 0.6 | | |
| 19 [11] | 10 | 20 | | | 0.47 | | |
| 20 [12] | 10 | 20 | | | 0.2 | | |
| 21 | 10 | | | 13 | | 2.5 | |
| 22 | 10 | | 20 | | | 2.5 | |
| 23 [13] | 10 | 20 | | | 0.13 | | |
| 24 [14] | 10 | 20 | | | 0.42 | | |
| 25 [15] | 10 | 20 | | | 0.6 | | |
| 26 [16] | 10 | 20 | | | 0.13 | | |
| 27 [17] | 10 | 20 | | | 0.42 | | |
| 28 [18] | 10 | 20 | | | 0.6 | | |
| 29 [19] | 10 | 20 | | | 0.22 | | |
| 30 [20] | 10 | 20 | | | 0.15 | | |
| 31 [21] | 10 | 20 | | | 0.44 | | |
| 32 [22] | 10 | 20 | | | 0.6 | | |
| 33 [23] | 10 | 20 | | | | | |
| 34 [24] | 10 | 20 | | | | | 1.0 |

*phosphate buffer.
[1] with 0% poloxamer;
[2] with 0.1 wt % PluronicF127, the solution passing USP elution tests before and after one autoclave and showing no biological reactivity;
[3] with 0.5 mM EDTA;
[4] with 0.1% PluronicF127 and 0.5 mM EDTA;
[5] with 0.1 wt % pluronic and 0.5 mM EDTA;
[6] with 0.0045 wt % Poloxamer108 and 0.5 mM EDTA;
[7] with 0.0045 wt % Poloxamer108;
[8] with 0.5 mM EDTA;
[9] with 0.0045 wt % Poloxamer108;
[10] with 5 mM Mg(NO$_3$)$_2$ and 0.0045% Poloxaner108;
[11] with 20 mM Mg(NO$_3$)$_2$ and 0.0045% Poloxamer108;
[12] with 50 mM Mg(NO$_3$)$_2$ and 0.0045% Poloxamer108;
[13] with 101 mM NH$_4$Cl and 0.0045 wt % Poloxamer108;
[14] with 50 mM NH$_4$Cl and 0.0045 wt % Poloxamer108;
[15] with 20 mM NH$_4$Cl and 0.0045 wt % Poloxamer108;
[16] with 100 mM NH$_4$NO$_3$ and 0.0045 wt % Poloxamer108;
[17] with 50 mM NH$_4$NO$_3$ and 0.0045 wt % Poloxamer108;
[18] with 20 mM NH$_4$NO$_3$ and 0.0045 wt % Poloxamer108;
[19] with 50 mM Mg(NO$_3$)$_2$
[20] with 100 mM KNO$_3$ and 0.0045 wt % Poloxamer108;
[21] with 50 mM KNO$_3$ and 0.0045 wt % Poloxamer108;
[22] with 20 mM KNO$_3$ and 0.0045 wt % Poloxamer108;
[23] with 125 mM KNO$_3$ and 0.0045 wt % Poloxamer108;
[24] with 55 mM KNO$_3$.

The above prepared solutions are tested to examine their effects on the autoclave (AC)-induced haziness of films prepared in Example 3. The results are shown in Table 2.

TABLE 2

| Solution | pH | mOsm | $T_0$(500 nm)% | $T_1$(500 nm)% |
|---|---|---|---|---|
| DI water | | | 99 | 99 |
| 1 | 7.4 | 321 | 98 | 87 |
| 2 | 7.4 | 324 | 99 | 85 |
| 3 | 7.2 | 313 | 100 | 90 |
| 4 | 7.1 | 331 | 99 | 84 |
| 5 | 7 | 282 | 99 | 99 |
| 6 | 7 | 308 | 99 | 99 |
| 7 | 6.9 | 285 | 100 | 98 |
| 8 | 7 | 304 | 98 | 99 |
| 9 | 6.9 | 306 | 100 | 96 |
| 10 | 7 | 309 | 100 | 98 |
| 11 | 7.7 | 291 | 99 | 100 |
| 12 | 7.7 | 321 | 99 | 99 |
| 13 | 7 | 307 | 99 | 98 |
| 14 | 7 | 308 | 99 | 100 |
| 15 | 7.5 | 307 | 99 | 99 |
| 16 | 7.5 | 293 | 98 | 100 |
| 17 | 7 | 314 | 99 | 99 |
| 18 | 7.2 | 278 | 97 | 91 |
| 19 | 7.1 | 274 | 98 | 94 |
| 20 | 6.8 | 267 | 100 | 97 |
| 21 | 7.1 | 314 | 100 | 98 |
| 22 | 7 | 313 | 100 | 99 |
| 23 | 7.3 | 301 | 99 | 97 |
| 24 | 7.4 | 302 | 98 | 97 |
| 25 | 7.5 | 306 | 98 | 93 |
| 26 | 7.3 | 295 | 98 | 98 |
| 27 | 7.4 | 302 | 98 | 96 |
| 28 | 7.5 | 305 | 99 | 95 |
| 29 | 7.1 | 270 | 99 | 97 |
| 30 | 7.2 | 295 | 100 | 88 |
| 31 | 7.2 | 300 | 100 | 85 |
| 32 | 7.3 | 304 | 100 | 89 |
| 33 | 7.3 | 296 | 99 | 92 |
| 34 | 7.3 | 294 | 100 | 93 |

The results indicate that autoclave-induced haziness of PEG-polyurea hydrogel material can be reduced by lowering the concentration of citrate buffer, phosphate buffer, and/or sodium chloride and by adding glycerol or sorbitol or the like in the solution. It appears that the citrate can facilitate the phase separation in PEG-polyurea hydrogel. But, since the citrate is needed to reduce the susceptibility to oxidation degradation of PEG-polyurea, one may need to add glycerol or sorbitol or the like in the solution to avert the phase separation and also may need to reduce (or eliminate) the concentrations of phosphate and chloride. When very high concentrations of certain ions, such as $NO_3^-$ and $NH_4^+$, are present in the solution, autoclave-induced haziness of PEG-polyurea hydrogel material may also be reduced.

Surface tensions of solutions 9 and 14 are determined to be about 56.6 mN/m and 50.1 mN/m respectively. The surface tension of a phosphate buffered saline with 0.0045 wt % Poloxamer 108 is determined to be 54.4 mN/m. These results indicated that glycerol can lower the surface tension of a solution and that with the presence of glycerol, a solution may not need to have a surfactant to lower the surface tension any further to minimize meniscus formation in a polypropylene lens package.

EXAMPLE 6

Dark Field Light Microscopy (DFLM) is used to evaluate the autoclave-induced haziness of PEG-containing polyurea contact lenses as follows. A lens is immersed in 0.2 μm-filtered phosphate buffer saline in a quartz Petri dish which is placed on a DFLM stand with ring lamp and variable height adjustment. Digital black and white DFLM images are taken by using a Pulnix CCD. The light source is Fostec or a comparable variable intensity light source. Calibration of light source intensity is conducted each time lenses are imaged by using a standard of overlapping plastic cover-slips. The overlapping regions of the cover-slips result in different density/light scattering regions that are used to adjust the light intensity to the same level each time the light source is turned on. Set the light source to an appropriate level for the samples being tested (nominal settings are just below 70% of max voltage (red mark) and 5 aperture on the Fostec light source. The median of each peak of the standard histogram was recorded. Image Pro Plus image analysis software, v.4.5.0.19 is used to analyze DFLM images of lenses under test. Set the software settings: Brightness to 35; Contrast to 35; Hue to 0; Saturation to 32; Upper Voltage to 0; and Lower Voltage to 0. Check the 8-bit data Gray-Scale Acquisition check box. Save the software settings as a *.vpf file. In acquired digital images, each pixel has a grayscale number. The haziness is expressed by averaging the grayscale numbers of all pixels in an area (e.g., a whole lens or the lenticular zone or optical zone of a lens). It is believed that since the dark-field setup involves scattered light, dark-field data could provide the worst-case estimate of haziness.

Several batches of PEG-polyurea prepolymers were prepared according to Example 1 or 2. Some lens formulations include a mold releasing agent PVP. Contact lenses with optical power of −10 diptors are prepared from a PEG-polyurea prepolymer according to procedure described in Example 4. The autoclave-induced haziness of the prepared lenses are reported in Table 3 (the values of haziness are averages; ocular region is ~8 mm diameter around the center and the remaining part is lenticular region), together with some commercially available contact lenses.

TABLE 3*[#]

| | Haziness | | |
|---|---|---|---|
| Lenses | Ocular | Lenticular | Solution |
| A | 15-50 | 15-50 | CPBS |
| B | 20 | 27 | CPBS |
| B | 1 | 5 | CPTG |
| C | 73 | 80 | CPBS |
| D | 24 | 30 | CPBS |
| C | 1 | 1 | CPTG |
| D | 1 | 1 | CPTG |
| C | 8 | 15 | CPTG[1] |
| C[2] | 7 | 14[3] | CPTG[1] |
| Acuvue-Advance | 12 | 20 | PBS |
| CSI | 90 | 90 | PBS |

*CPBS contains 10 mM citrate, 20 mM phosphate buffer, and 0.7% by weight NaCl; CPTG contains 10 mM citrate, 14 mM phosphate buffer, 29 mM TRIS, and 2.1% by weight of glycerol; PBS is phosphate buffered saline.
[#]Only lenses A are prepared from PEG-polyurea prepolymer prepared in Example 1.
[1]The lens formulation contains 2% PVP as mold releasing agent.
[2]Toric contact lenses with a design similar to O₂OPTIX Toric.
[3]There are a few spots of about 2-2.5 mm in size, which have about 55% haziness.

The results show that the autoclave-induced haziness can be reduced or eliminated by using a citrate/phosphate/TRIS/glycerol solution (solution 7 in Example 5). It is found that a mold releasing agent present in lens formulation may slightly increase the haziness of the PEG-polyurea lenses.

EXAMPLE 7

Various solutions (solutions 3-10 in Table 1) are studied to determine their effects on the cloudy point of a solution of PEG-polyurea prepolymer prepared in Example 2. The results are shown in Table 4. Solutions 3-10 in Table 1 are also studied to determine their effects on the autoclave (AC)-induced haziness of films prepared in Example 3

TABLE 4

| Solution | $T_0$(500 nm)% | $T_1$(500 nm)% | Cloudy Point*, ° C. |
|---|---|---|---|
| DI water | 99 | 99 | 57 |
| 3 | 100 | 90 | 49 |
| 4 | 99 | 84 | 45 |
| 5 | 99 | 99 | 54 |
| 6 | 99 | 99 | 52 |
| 7 | 100 | 98 | 51 |
| 8 | 98 | 99 | 54 |
| 9 | 100 | 96 | 54 |
| 10 | 100 | 98 | 54 |

*Cloudy points of PEG-polyurea prepolymer dissolved in a testing solution.

It is found that solution with a high concentration of citrate (solution 4) or phosphate (solution 3) can not only lower the cloudy point of PEG-polyurea prepolymer but also increase the haziness (i.e., lower T % at 550 nm) of a film made from the PEG-polyurea prepolymer. By lowering citrate concentration to 10 mM and phosphate concentration below 15 mM, one can have a relative higher cloudy points and a minimal or no haziness (T %>98%) of the film. Good results are observed with the 10 mM citrate-14 mM phosphate-29 mM TRIS buffer systems with 2.1% glycerol.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Therefore, the spirit and scope of the appended claims should not be limited to the description of the preferred versions contained therein.

What is claimed is:

1. An ophthalmic product, comprising a sealed container which has been subjected to sterilization by autoclave, wherein the sealed container includes an aqueous solution and an ophthalmic device immersed in the aqueous solution, wherein the ophthalmic device is made of a poly(oxyalkylene)-containing polymeric material, wherein the aqueous solution comprising:
an alpha-oxo-multi-acid or salt thereof in an amount sufficient to have a reduced susceptibility to oxidative degradation of the poly(oxyalkylene)-containing polymeric material;
one or more buffer agents selected from group consisting of TRIS (tris(hydroxymethyl)aminomethane), bis-aminopolyols, triethanolamine, ACES (N-(2-hydroxyethyl)-2-aminoethanesulfonic acid), BES (N,N-Bis(2-hydroxyethyl)-2-aminoethanesulfonic acid), HEPES (4-(2-hydroxyethyl)-1-piperazineethanesulfonic acid), MES (2-(N-morpholino)ethanesulfonic acid), MOPS 3-[N-morpholino]-propanesulfonic acid, PIPES (piperazine-N,N'-bis(2-ethanesulfonic acid), TES (N-[Tris(hydroxymethyl)methyl]-2-aminoethanesulfonic acid), and salts thereof;
an organic tonicity-adjusting agent in an amount sufficient to provide an osmolarity of from about 200 to about 450 milli-osmole in 1000 ml (unit: mosm/l), wherein the organic tonicity-adjusting agent is selected from the group consisting of glycerol, sorbitol, xylitol, mannitol, propylene glycol, polyethylene glycol (PEG) with a molecular weight of about 400 Da or less, and mixtures thereof,
wherein the aqueous solution has a pH of from about 5.5 to about 8.5, provided that the aqueous solution include phosphate buffer at a concentration of 15 mM or less and about 5000 ppm sodium chloride.

2. The ophthalmic product of claim 1, wherein the one or more buffer agents are selected from the group consisting of TRIS, bis-aminopolyols, and salts thereof, wherein the bis-aminopolyols have formula (I)

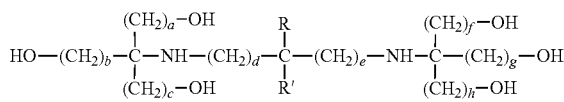

wherein a, b, c, d, e, f, g, and h are independently an integer from 1 to 6; and R and R' are independently selected from the group consisting of —H, —CH$_3$, —(CH$_2$)$_{2-6}$—H, and —(CH$_2$)$_{1-6}$—OH.

3. The ophthalmic product of claim 2, wherein the one or more buffer agents are TRIS and salt thereof.

4. The ophthalmic product of claim 2, wherein the one or more buffer agents are 1,3-bis(tris[hydroxymethyl]methylamino)propane and salt thereof.

5. The ophthalmic product of claim 2, wherein the alpha-oxo-multi-acid is citric acid or malic acid.

6. The ophthalmic product of claim 2, wherein the ophthalmic device is a hydrogel contact lens which is composed of a poly(oxyalkylene)-containing polyurea material.

7. The ophthalmic product of claim 2, wherein the solution contains less than 1000 ppm chloride ion.

8. The ophthalmic product of claim 2, wherein the solution contains 10 mM or less of phosphate buffer.

9. The ophthalmic product of claim 2, wherein the solution imparts a reduced autoclave-induced haziness to the ophthalmic device, wherein the reduced autoclave-induced haziness by having less than 10% autoclave-induced reduction in light transmissibility at 500 nm.

10. The ophthalmic product of claim 2, wherein the solution imparts a reduced autoclave-induced haziness to the ophthalmic device, wherein the reduced autoclave-induced haziness having less than 5% autoclave-induced reduction in light transmissibility at 500 nm.

11. The ophthalmic product of claim 2, wherein the solution has a surface tension of 50 mN/m or smaller.

12. An ophthalmic product, comprising a sealed container which has been subjected to sterilization by autoclave, wherein the sealed container includes an aqueous solution and an ophthalmic device immersed in the aqueous solution, wherein the ophthalmic device is composed of a hydrogel material, wherein the aqueous solution includes an organic tonicity-adjusting agent in an amount sufficient to provide an osmolarity of from about 200 to about 450 milli-osmole in 1000 ml (unit: mosm/l) and one or more buffer agents selected from group consisting of tris-(hydroxymethyl)aminomethane) (TRIS), bis-aminopolyols, triethanolamine, N-(2-hydroxyethyl)-2-aminoethanesulfonic acid (ACES), N,N-Bis(2-hydroxyethyl)-2-aminoethanesulfonic acid (BES), 4-(2-hydroxyethyl)-1-piperazineethanesulfonic acid (HEPES), 2-(N-morpholino)ethanesulfonic acid (MES), 3-[N-morpholino]-propanesulfonic acid (MOPS), piperazine-N,N'-bis(2-ethanesulfonic acid) (PIPES), N-tris(hydroxymethyl)methyl-2-aminoethanesulfonic acid (TES), and salts thereof, wherein the organic tonicity-adjusting agent is selected from the group consisting of glycerol, sorbitol, xylitol, mannitol, propylene glycol, polyethylene glycol (PEG) with a molecular weight of about 400 Da or less, and mixtures thereof, wherein the aqueous solution has a pH of from about 5.5 to about 8.5, wherein the aqueous solution include phosphate buffer at a concentration of about 15 mM or less and about 5000 ppm sodium chloride so that the solution imparts a reduced autoclave-induced haziness to the ophthalmic device, wherein the reduced autoclave-induced haziness having less than about 5% autoclave-induced reduction in light transmissibility at 500 nm.

\* \* \* \* \*